United States Patent
Apell et al.

(10) Patent No.: US 9,672,420 B2
(45) Date of Patent: Jun. 6, 2017

(54) METHOD FOR A MEDICATION DISPENSER TO OBTAIN INFORMATION FROM A MEDICATION PACKAGE, AND MEDICATION DISPENSER

(71) Applicant: EVONDOS OY, Salo (FI)

(72) Inventors: Mika Apell, Turku (FI); Jyrki Niinistö, Halikko (FI)

(73) Assignee: EVONDOS OY, Salo (FI)

( * ) Notice: Subject to any disclaimer, the term of this patent is extended or adjusted under 35 U.S.C. 154(b) by 286 days.

(21) Appl. No.: 14/015,268

(22) Filed: Aug. 30, 2013

(65) Prior Publication Data
US 2014/0067114 A1 Mar. 6, 2014

(30) Foreign Application Priority Data
Aug. 31, 2012 (EP) .................................... 12182648

(51) Int. Cl.
| | | |
|---|---|---|
| *G06F 19/00* | (2011.01) | |
| *G06K 9/00* | (2006.01) | |
| *A61J 7/00* | (2006.01) | |
| *A61J 7/04* | (2006.01) | |
| *B26D 5/00* | (2006.01) | |
| *G07F 11/68* | (2006.01) | |
| *G07F 17/00* | (2006.01) | |
| *B26D 5/20* | (2006.01) | |
| *B65B 57/00* | (2006.01) | |

(Continued)

(52) U.S. Cl.
CPC ........ *G06K 9/00469* (2013.01); *A61J 7/0076* (2013.01); *A61J 7/04* (2013.01); *B26D 5/007* (2013.01); *B26D 5/20* (2013.01); *B65B 57/00* (2013.01); *B65B 61/06* (2013.01); *B65B 61/28* (2013.01); *G06F 19/3462* (2013.01); *G07F 11/68* (2013.01); *G07F 17/0092* (2013.01); *A61J 2205/30* (2013.01)

(58) Field of Classification Search
CPC ........ A61J 7/0076; A61J 7/04; A61J 2205/30; B26D 5/007; B26D 5/20
USPC .................................................. 700/236, 244
See application file for complete search history.

(56) References Cited

U.S. PATENT DOCUMENTS

| | | |
|---|---|---|
| 4,971,221 A | 11/1990 | Urquhart et al. |
| 5,097,982 A | 3/1992 | Kedem et al. |

(Continued)

FOREIGN PATENT DOCUMENTS

| | | |
|---|---|---|
| EP | 2 026 298 A1 | 2/2009 |
| EP | 2 457 550 A1 | 5/2012 |

(Continued)

*Primary Examiner* — Michael K Collins
(74) *Attorney, Agent, or Firm* — Buchanan Ingersoll & Rooney PC

(57) ABSTRACT

The present invention relates to a method for obtaining information from a medication package. In the method, an image of the medication package is provided, the image is analyzed to determine positions and formats of patterns in the image, a layout, which has similar pattern formats in the same positions as the image, is selected from a set of layouts stored in the medication dispenser, the selected layout defining the type of information for each pattern in the image, and the information contained in at least one of the patterns of the image is interpreted by linking the content of the pattern to the type of information defined in the selected layout. The invention also relates to a medication dispenser.

17 Claims, 3 Drawing Sheets

(51) Int. Cl.
  *B65B 61/06* (2006.01)
  *B65B 61/28* (2006.01)

(56) References Cited

U.S. PATENT DOCUMENTS

| | | | |
|---|---|---|---|
| 5,805,051 | A | 9/1998 | Herrmann et al. |
| 6,529,446 | B1 | 3/2003 | de la Huerga |
| 7,264,136 | B2 | 9/2007 | Willoughby et al. |
| 7,792,349 | B2 | 9/2010 | Van Den Brink |
| 7,828,147 | B2* | 11/2010 | Caracciolo ......... G06F 19/3462 206/530 |
| 8,019,417 | B2 | 9/2011 | Bornzin et al. |
| 8,019,471 | B2* | 9/2011 | Bogash ............ G06F 19/3462 700/232 |
| 8,600,548 | B2* | 12/2013 | Bossi ............... G06F 19/3462 700/231 |
| 8,798,367 | B2* | 8/2014 | Ellis ................. G06F 19/3462 382/117 |
| 9,101,530 | B2* | 8/2015 | Wilson ................ A61J 1/035 |
| 2002/0027507 | A1 | 3/2002 | Yarin et al. |
| 2002/0067270 | A1 | 6/2002 | Yarin et al. |
| 2003/0099158 | A1 | 5/2003 | De la Huerga |
| 2004/0117062 | A1 | 6/2004 | Bonney et al. |
| 2004/0158350 | A1 | 8/2004 | Ostergaard et al. |
| 2005/0041531 | A1 | 2/2005 | Sekura |
| 2005/0240305 | A1* | 10/2005 | Bogash ............ G06F 19/3462 700/242 |
| 2005/0268909 | A1 | 12/2005 | Bonney et al. |
| 2006/0071011 | A1 | 4/2006 | Varvarelis et al. |
| 2007/0043469 | A1 | 2/2007 | Draper |
| 2007/0185615 | A1 | 8/2007 | Bossi et al. |
| 2007/0260487 | A1 | 11/2007 | Bartfeld et al. |
| 2008/0059228 | A1 | 3/2008 | Bossi et al. |
| 2008/0119958 | A1* | 5/2008 | Bear ..................... A61J 7/0481 700/244 |
| 2008/0215289 | A1 | 9/2008 | Sekura |
| 2008/0290106 | A1 | 11/2008 | van der Klaauw et al. |
| 2009/0030730 | A1 | 1/2009 | Dullemen et al. |
| 2009/0198208 | A1 | 8/2009 | Stavsky et al. |
| 2010/0045466 | A1 | 2/2010 | Sekura |
| 2010/0127073 | A1 | 5/2010 | van Esch |
| 2010/0215231 | A1 | 8/2010 | Bartfeld et al. |
| 2010/0249997 | A1 | 9/2010 | Greyshock et al. |
| 2010/0298975 | A1* | 11/2010 | Heath ................... A61J 1/035 700/237 |
| 2010/0305967 | A1 | 12/2010 | Daya et al. |
| 2011/0193705 | A1 | 8/2011 | Sekura |
| 2012/0004770 | A1 | 1/2012 | Ooyen et al. |
| 2012/0081225 | A1 | 4/2012 | Waugh et al. |
| 2012/0083666 | A1 | 4/2012 | Waugh et al. |
| 2012/0126958 | A1 | 5/2012 | Kim et al. |
| 2012/0199650 | A1 | 8/2012 | Horst et al. |
| 2012/0273087 | A1 | 11/2012 | Stavsky et al. |
| 2013/0169798 | A1 | 7/2013 | Pellerin et al. |
| 2013/0195326 | A1* | 8/2013 | Bear ..................... A61J 7/0076 382/128 |
| 2014/0067114 | A1* | 3/2014 | Apell ..................... B65B 57/00 700/244 |
| 2014/0163474 | A1* | 6/2014 | Draper ............ A61M 5/31551 604/189 |
| 2014/0172162 | A1* | 6/2014 | Draper ............ A61M 5/31551 700/243 |

FOREIGN PATENT DOCUMENTS

| | | |
|---|---|---|
| WO | WO 91/04726 A1 | 4/1991 |
| WO | WO 00/7538 A2 | 2/2000 |
| WO | WO 01/47466 A1 | 7/2001 |
| WO | WO 02/078593 A2 | 10/2002 |
| WO | WO 03/001337 A2 | 1/2003 |
| WO | WO 2007/129318 A2 | 11/2007 |
| WO | WO 2008/135823 A1 | 11/2008 |
| WO | WO 2009/095904 A1 | 8/2009 |
| WO | WO 2011/042840 A1 | 4/2011 |
| WO | WO 2011/112606 A1 | 9/2011 |
| WO | WO 2011/123931 A1 | 10/2011 |
| WO | WO 2011/123933 A1 | 10/2011 |
| WO | WO 2012/007411 A1 | 1/2012 |

\* cited by examiner

METHOD FOR A MEDICATION DISPENSER TO OBTAIN INFORMATION FROM A MEDICATION PACKAGE, AND MEDICATION DISPENSER

TECHNICAL FIELD OF THE INVENTION

The present invention relates to a method for a medication dispenser to obtain information from a medication package and to a medication dispenser according to the preambles of the appended independent claims.

BACKGROUND OF THE INVENTION

Various devices are known for assisting a patient in complying with his/her medical regimen. The most sophisticated devices are so-called medication dispensers, which dispense medication packages at prescribed times to provide the patient with the proper dosage of medications. The medications are prepackaged by licensed pharmacies into packages according to the medical regimen of the patient. The medication packages have labels that contain information about the patient, the content of the package, and the time of the dosage.

Typically, the medication packages are arranged as a strip, which is inserted into a container of the medication dispenser either by the patient or a caregiver of the patient. The medication dispenser delivers the medication packages to the patient one package at a time according to the information provided by the labels of the packages. The medication dispenser typically allows the dispensation of medications to be monitored and controlled so that the patient, the caregiver or any other person having access to the apparatus can be assured that the patient is taking the medications as prescribed.

A problem associated with medication dispensers of the prior art relates to their dependence on a package type and format of the printed data. The known medication dispensers can only handle medication packages having a specific package type with fixed format of printed data. If a wrong package type is applied in a medication dispenser, information from a medication package cannot be obtained or is only partly obtained.

OBJECTIVES OF THE INVENTION

It is the main objective of the present invention to reduce or even eliminate prior art problems presented above.

It is an objective of the present invention to provide a method and a medication dispenser enabling to obtain information from a medication package. It is also an objective of the invention to provide a method and a medication dispenser enabling to obtain information from different types of medication packages.

In order to realise the above-mentioned objectives, the method and the medication dispenser according to the invention are characterised by what is presented in the characterising parts of the appended independent claims. Advantageous embodiments of the invention are described in the dependent claims.

DESCRIPTION OF THE INVENTION

A typical method according to the invention for a medication dispenser to obtain information from a medication package comprises providing an image of the medication package, analysing the image to determine positions and formats of patterns in the image, selecting a layout, which has similar pattern formats in the same positions as the image, from a set of layouts stored in the medication dispenser, the selected layout defining the type of information for each pattern in the image, and interpreting the information contained in at least one of the patterns of the image by linking the content of the pattern to the type of information defined in the selected layout.

By a medication package is meant a package, such as a bag or pouch that contains medications to be taken at a certain predetermined time. The medication package can be a separate package, or be part of a strip that contains a plurality of medication packages attached to each other in time order. Typically, the medication packages of a strip have the same package type, so that once the layout has been selected for the first medication package of the strip, the same layout can be used for the rest of the medication packages.

The medication package has a label that contains package-related information. The information is embedded into patterns, which can have different formats, such as text, or a one- or two-dimensional bar code. Each pattern contains a certain type of information. The information type can be, for example, identification information of the person to whom the medication package is meant to be dispensed, such as his/her name or social security number, and/or information related to the medical regimen of the person, such as the content of the package, and the taking time of the medications.

The image of the medication package contains the patterns of the label, but it may also contain other patterns of the medication package, such as a pattern of a seam between two medication packages. The patterns of the image as well as their positions and formats are preferably determined using pattern recognition techniques. The image of the medication package is preferably provided by capturing with a camera an image of the medication package.

The layouts are stored in a memory of the medication dispenser, from which memory the layout corresponding to the type of the medication package is selected. A layout represents a certain package type that can be applied in the medication dispenser. A layout defines the positions and formats of patterns that a certain package type has. It also defines the type of information for each pattern in the package type. The layout may define, for example, that at a certain position with a certain format is embedded the name of the patient, and that at another position with another format is embedded the taking time of the medications.

A layout may include information about the position of a seam relative to a package label, about the seam pattern parameters like the width of the seam area including glued areas and perforation, or only about the width of each glued area. It may also include information about the processing parameters, such as environment parameters including lighting intensity, direction or wavelength, or digital filters and their parameters for a specific strip. The seam specific information in a layout can be updated based on the information that has been gathered during the processing to optimise the seam detection accuracy.

In a method according to the invention the type of the medication package is recognised by comparing the image of the medication package to the layouts stored in the medication dispenser. First, positions and formats of the patterns in the image are determined. Then, the positions and formats are compared to the layouts in order to find the layout which has similar formats in the same positions as the image. The layout defines the type of information for each pattern in the image so that the information embedded into the patterns can be interpreted. Preferably, the interpreted information contains the taking time of the medications, so that the medication dispenser is able to dispense the medications to the patient at the correct time.

The method according to the invention enables to obtain information from different types of medication packages, whereby the use of the medication dispenser is not limited to a specific package type.

According to an embodiment of the invention the step of providing an image of the medication package comprises capturing with a camera at least one image of the medication package, and combining the at least one image into a single image. The number of images that are captured can vary, depending for example on the size of the medication package. Typically, one or just a few images are captured, but in some cases the number of captured images can be higher, for example, 5-10, 10-20, 20-30, or even more than 30.

Between the capturing of images, the camera and/or the medication package can be moved and/or the lighting conditions can be changed, in order to enhance recognition accuracy. Several image processing techniques can be utilised for combining the images, for example, HDR (High Dynamic Range) or stereo imaging techniques.

According to an embodiment of the invention the method comprises moving the medication package across an imaging area of the camera between the capturing of the images.

By the imaging area is meant the area of which the camera is capable of capturing images. The imaging area is preferably rectangular and the aspect ratio is typical to image sensors, for example 16:9 or 4:3. Preferably, the camera is positioned in such a manner that the medication package fits in the imaging area. If the medication package is wider than the imaging area, the camera can be moved in a direction of the width of the package and a plurality of images can be captured and then combined.

The medication package can be moved across the imaging area of the camera continuously or discontinuously. The images are preferably captured when the medication package is not moving. Once the medication package is moved to a new place, one or more images may be taken of the package. Images may also be taken while the medication package is being moved. The medication package may be moved in one direction, or back and forth across the imaging area. Between the capturing of images, imaging conditions may be changed. It is also possible to move the camera in a direction of the width of the strip between the capturing of images.

The medication package may be moved in steps having a fixed length or in steps having differing lengths. For example, the length of the steps may be arranged to decrease as the recognition process proceeds. The length of the steps can be, for example, 1-5 mm, 5-10 mm, 10-30 mm, or 30-100 mm. The medication package may also be moved in steps when transferring the first medication package of the strip to the imaging area or moving the strip from one seam to another. In these cases long steps are usually used. On the other hand, short steps are needed for finetuning the medication package to the imaging area of the camera or the seam to the cutter of the medication dispenser.

According to an embodiment of the invention the method comprises illuminating with at least one light source the medication package. By illuminating the medication package, the image quality can be increased. In many cases the use of at least two light sources is preferable because the light can then be directed to the medication package from different directions. Preferably, the light sources are LEDs.

According to an embodiment of the invention the method comprises changing the intensity and/or the direction and/or the wavelength of the lighting. The intensity and/or the direction and/or the wavelength of the lighting may be changed between the capturing of images in order to increase the image quality.

Lighting from the sides or back of the medication package highlights the patterns from other parts in the image of the medication package. Large contrast differences are formed, for example, on a seam area between two consecutive packages in a strip. The seam forms a certain pattern including a non-flat dotted perforation and a blurry glued area. Especially the side lighting is useful for highlighting seam patterns in the strip. Lighting from different directions can be dynamically adjusted for different strip types to find an optimal lighting condition for a specific strip. The dynamical adjustment can be automatically run when the medication dispenser has been refilled and another strip type has been detected.

According to an embodiment of the invention the method comprises vibrating and/or straightening the medication package that is located in the imaging area. A purpose of the vibrating and/or straightening is to reorganise medication pills lying on each other so that the medication package becomes as flat as possible. Another purpose of the straightening is to keep the medication package straight during imaging. Preferably, the medication package is vibrated and/or straightened before capturing each image.

According to an embodiment of the invention the method comprises changing the position of the camera. The position of the camera can be changed between the capturing of the images. A purpose of moving the camera is to enable scanning of the package surface in a direction of the width of the medication package. This enables taking several images of the uneven surface and combining them to enhance image quality for image processing. Preferably, several pictures are taken, if recognition faults are detected.

According to an embodiment of the invention the step of providing an image of the medication package comprises receiving the image from a server over a communications network.

According to an embodiment of the invention the method comprises, if an error occurs in the step of selecting a layout, sending the image to a server over a communications network, generating, at the server, a new layout based on the image, and sending the new layout to the medication dispenser over a communications network.

The generation of a new layout may be based on the recognised patterns in the image and information available in the medication dispenser and/or the server. The information used may have been fed, for example, to the medication dispenser during refilling, from which the information is transmitted to the server. At the server, the image is analysed to find text and one- or two-dimensional bar code fields. These fields are interpreted to data strings. The data strings are further analysed based on the information in the server and/or received from the medication dispenser. This information may include, for example, a patient name, a patient ID, current date and time, medication history and the taking time of the last medication package in the preceding strip. Based on this information, for example, the patient name, patient ID and medication taking time are searched from the data strings. If matching strings or parts of the strings are found, a preliminary layout is generated based on them and the next two medication packages are processed by using the preliminary layout. Fixed data, such as the patient name and patient ID, should be the same in each medication package.

The detected taking times should be in consecutive order and should follow closely the medication history. If a new layout cannot be generated with the available information, more information, such as the taking time of the medication package and format of the date and time, can be asked. Based on this additional information the layout generation is restarted. The generated layout is saved in a layout database from which the new layout as well as the other layouts can be downloaded to medication dispensers.

According to an embodiment of the invention the method comprises giving a notification, if an error occurs in the step of selecting a layout. The patient, the caregiver or any other authorised person may be notified with an audio or visual signal. The patient may be notified, for example, with an alarm that is played using a loudspeaker, or visually using a lamp or a display. The caregiver or any other authorised person may be notified, for example, with a message sent over a communications network to a mobile device. The message can be, for example, an SMS (short message service) or MMS (multimedia messaging service) message.

According to an embodiment of the invention one or more of the steps of analysing the image, selecting a layout and interpreting the information are carried out at a server that is communicatively connected to the medication dispenser over a communications network.

In a strip of medication packages, a seam between two packages typically consists of elements, such as perforation and/or glued areas, which can be distinguished from the other parts of the strip. Perforation and gluing affect the surface and transparency of the medication package. The package surface is flatter outside the perforation and glued areas, and the perforation is recognised as a series of dots. On the other hand, the transparency of a thin strip material is different on the seam area due to glue and perforation. They also differ from other detectable patterns on the package surface, because gluing and perforation is done from one edge of the strip to another edge of the strip.

Based on the selected layout, the pattern representing the seam can be identified. Another possibility to detect a seam between two consecutive packages in a strip is to determine the position of the seam directly from the image using pattern recognition. The image data is processed in vertical and/or horizontal directions to find a potential position for the seam. This can be based on detecting unprinted horizontal areas on the strip. During this process, digital filters and filter parameters used in pattern recognition can be changed.

The seam can be recognised using one or more images of the medication package. The images can be analysed separately, or the images can be combined to a single image before the analysis in order to enhance the image quality.

The position information of the seam is utilised in separating the medication package from the strip. Based on the position of the seam a cutting line is selected and the medication package is separated from the strip by cutting along the cutting line. The cutting line can be selected near the seam so that the medication package is opened upon cutting. The cutting line may alternatively be located on the seam, wherein the separated package remains closed. In this case, the medication package may, however, be partially opened by cutting a short opening near the seam.

The invention also relates to a medication dispenser. A typical medication dispenser according to the invention comprises a container for holding a medication package containing medications to be taken at a predetermined taking time, means for transferring the medication package from the container to an outlet of the medication dispenser, and means for providing an image of the medication package. The typical medication dispenser according to the invention further comprises a control unit that comprises means for analysing the image to determine positions and formats of patterns in the image, means for maintaining a set of layouts in the medication dispenser, means for selecting a layout, which has similar pattern formats in the same positions as the image, from the set of layouts, the selected layout defining the type of information for each pattern in the image, and means for interpreting the information contained in at least one of the patterns of the image by linking the content of the pattern to the type of information defined in the selected layout.

The purpose of the medication dispenser is to assist a patient in complying with the medical regimen by giving to the patient the right medications at the right times. The medications are packaged into medication packages, which have labels containing information relating to the package. Medication packages are inserted into the container by the patient or a caregiver of the patient, such as a nurse or a near relative. Preferably, the medication packages have been attached to each other in time order to form a strip from which the medication packages are separated and delivered to the patient at their taking times. The medication dispenser may comprise a cutter for separating the medication packages from the strip. Preferably, the cutter is arranged to also open the medication package, whereby the patient can easily take the medications out of the package.

The medication packages are transferred with the transfer means from the container to the outlet, from which the patient can take the medications. The outlet is preferably provided with a lid that may be lockable so that the access of the patient to the outlet can be prevented if desired. The transfer means may comprise for example one or more rollers, which are driven by means of an electric motor. The electric motor is controlled by the control unit.

The image of the medication package may be obtained from a server that is communicatively connected to the medication dispenser over a communications network. Preferably, however, the medication dispenser comprises a camera for capturing the image of the medication package. In this case, the medication package is transferred across the imaging area of the camera so that one or more images can be captured of the medication package. The camera is controlled by the control unit.

The control unit comprises a processor that is programmed to carry out the functions that are needed to operate the medication dispenser. Especially, the control unit comprises means for analysing the image to determine pattern positions and formats, means for selecting a layout that has similar pattern formats in the same positions as the image, and means for interpreting, based on the selected layout, the information contained in the patterns. The control unit also comprises a memory for maintaining the set of layouts.

The medication dispenser according to the invention may be configured, for example, to recognise a taking time and a seam position from the medication package by selecting a layout corresponding to the image of the medication package and, based on this layout, to determine the taking time and the seam position from the image. The medication package can then be cut at the correct position and delivered to the patient at the right time.

According to an embodiment of the invention the means for providing an image of the medication package comprises a camera.

According to an embodiment of the invention the medication dispenser comprises at least one light source arranged to illuminate the medication package.

According to an embodiment of the invention the means for providing an image of the medication package comprises a communications unit for receiving the image from a server over a communications network. The communications unit may also be arranged to transmit and receive other data.

According to an embodiment of the invention the medication dispenser comprises a detector arranged to detect the presence of the medication package in the container. When inserting a strip of medication packages into the container, the strip is detected by means of the detector. The detector may be arranged to produce a signal according to which the control unit controls the transfer means to transfer the head of the strip to the imaging area of the camera.

Being computer-related, it can be appreciated that the components disclosed herein may be implemented in hardware, software, or a combination of hardware and software. Software components may be in the form of computer-readable program code stored in a computer-readable storage medium such as memory, mass storage device, or removable storage device. For example, a computer-readable medium may comprise computer-readable code for performing the function of a particular component. Likewise, computer memory may be configured to include one or more components, which may then be executed by a processor. Components may be implemented separately in multiple modules or together in a single module.

The exemplary embodiments of the invention presented in this text are not interpreted to pose limitations to the applicability of the appended claims. The verb "to comprise" is used in this text as an open limitation that does not exclude the existence of also unrecited features. The features recited in the dependent claims are mutually freely combinable unless otherwise explicitly stated.

The exemplary embodiments presented in this text and their advantages relate by applicable parts to the method as well as the medication dispenser according to the invention, even though this is not always separately mentioned.

BRIEF DESCRIPTION OF THE DRAWINGS

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE DRAWINGS

Figure 1:
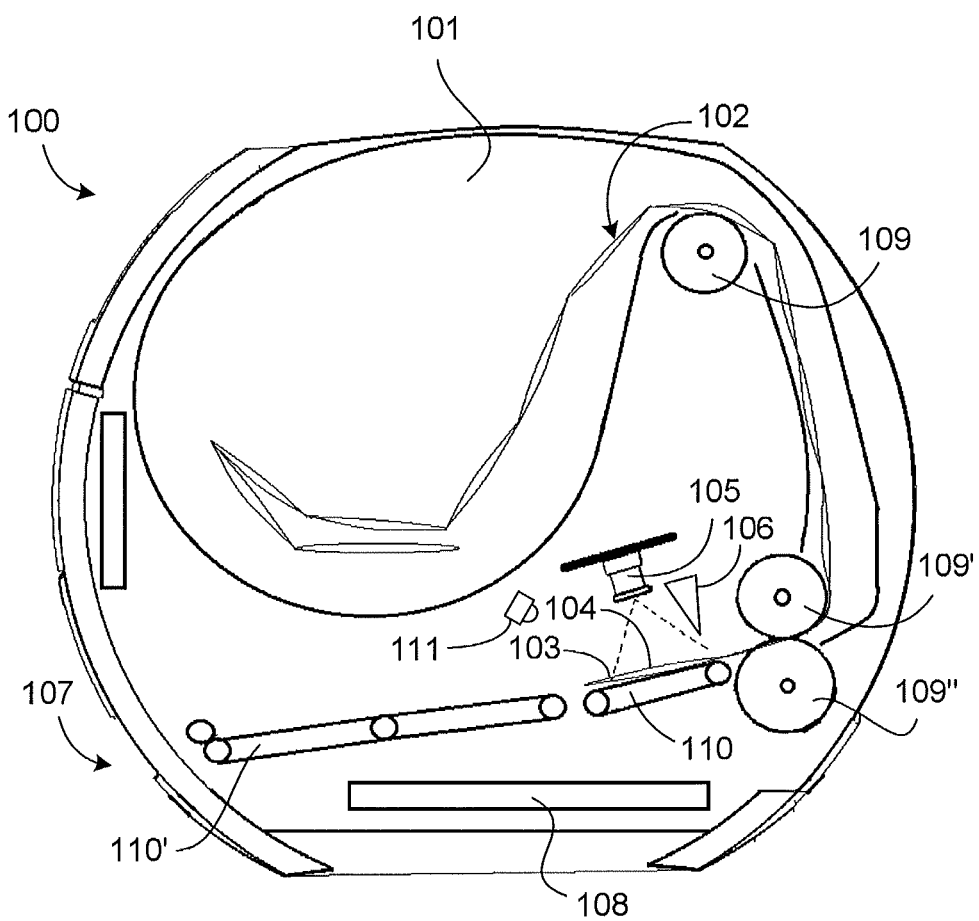
FIG. 1 illustrates a medication dispenser according to an embodiment of the invention.

FIG. 1 illustrates a medication dispenser according to an embodiment of the invention. The medication dispenser 100 comprises a container 101, which is arranged to receive a strip 102 of medication packages 103 that include medications to be taken at predetermined taking times. Each medication package 103 has a label 104 that contains information relating to the medication package 103. The medication dispenser 100 also comprises a camera 105, which is arranged to capture images of the part of the strip 102 that is located in an imaging area of the camera 105, and a cutter 106 that is used for separating the medication packages 103 from the strip 102. The medication dispenser 100 further comprises transfer means for transferring the medication packages 103 of the strip 102 from the container 101 to the imaging area of the camera 105 and then to an outlet 107 of the medication dispenser 100, and a control unit 108 arranged to control the camera 105, the cutter 106 and the transfer means.

The transfer means comprises rollers 109, 109', 109", which are arranged to transfer the strip 102 from the container 101 to the imaging area of the camera 105. The transfer means also comprises a roller table 110 that is arranged to transfer the strip across the imaging area, and a roller table 110' that is arranged to transfer the separated medication packages 103 to the outlet 107 of the medication dispenser 100. The medication dispenser 100 further comprises a light source 111 that is arranged to illuminate the part of the strip 102 that is located in the imaging area.

The control unit 108 comprises means for analysing the image of the medication package 103 to determine positions and formats of patterns in the image, means for maintaining a set of layouts in the medication dispenser 100, means for selecting a layout, which has similar pattern formats in the same positions as the image, from the set of layouts, the selected layout defining the type of information for each pattern in the image, and means for interpreting the information contained in at least one of the patterns of the image by linking the content of the pattern to the type of information defined in the selected layout.

Figure 2:
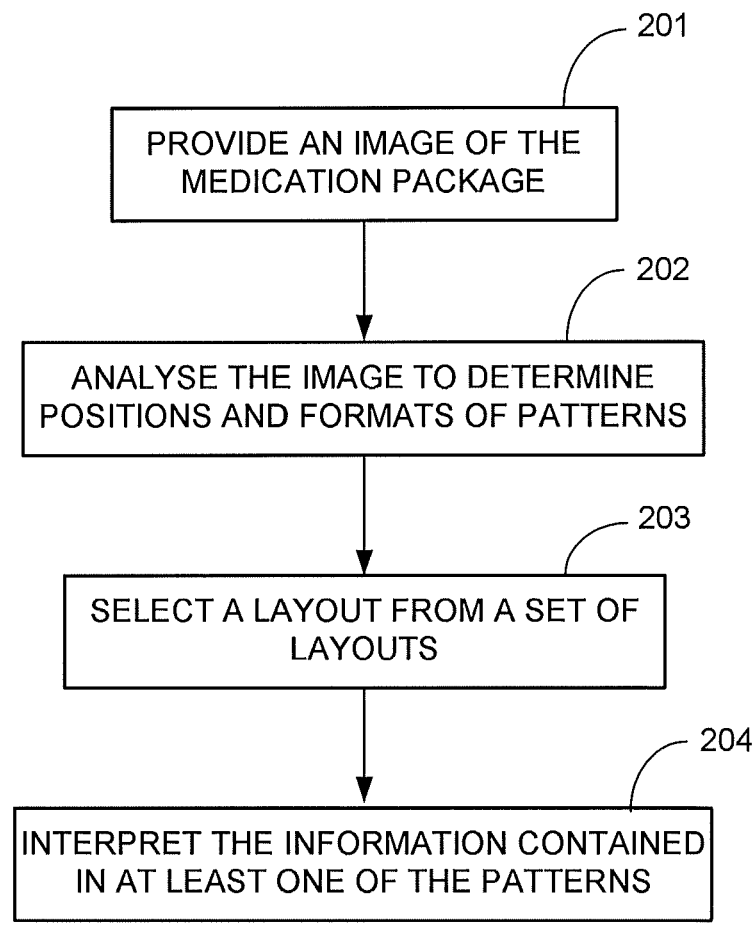
FIG. 2 illustrates a schematic diagram of a method according to an embodiment of the invention.

FIG. 2 illustrates a schematic diagram of a method according to an embodiment of the invention for obtaining information from a medication package.

At step 201 an image of the medication package 103 is provided to the medication dispenser 100. The image may be captured with the camera 105, or may be obtained from a server over a communications network.

At step 202 the image is analysed to determine positions and formats of patterns in the image.

At step 203 a layout, which has similar pattern formats in the same positions as the image, is selected from a set of layouts that are stored in the medication dispenser. The selected layout defines the type of information for each pattern in the image.

At step 204 the information contained in at least one of the patterns of the image is interpreted by linking the content of the pattern to the type of information defined in the selected layout.

Figure 3:
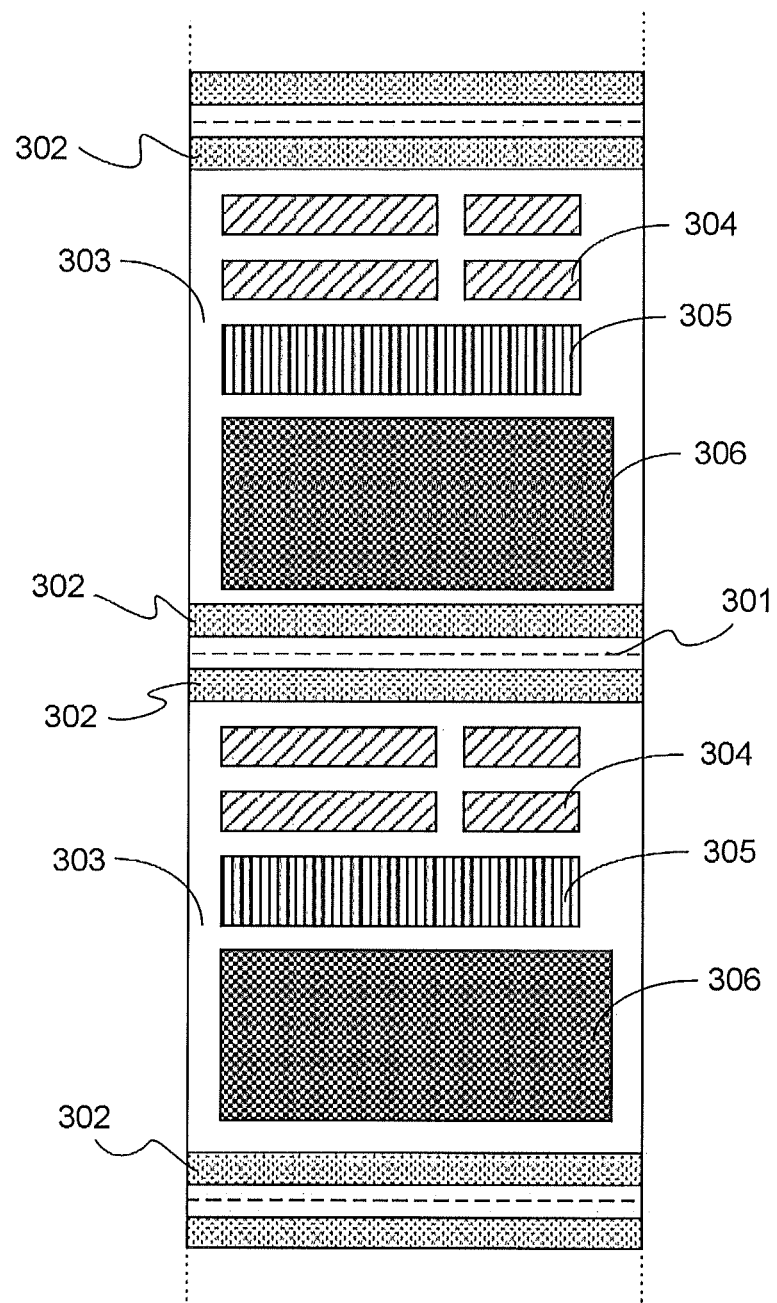
FIG. 3 illustrates a strip of medication packages.

FIG. 3 illustrates a strip of medication packages, wherein two full medication packages are shown. The medication packages are separated from one another by perforations 301, and both ends of each medication package adjacent to the perforation 301 are glued to close the medication package, as shown in 302. The label 303 of the package contains several patterns 304, 305, 306, comprising text, a one-dimensional bar code and a two-dimensional bar code, respectively. The patterns 304, 305, 306 are organised according to a pre-determined layout.

Only advantageous exemplary embodiments of the invention are described in the figures. It is clear to a person skilled in the art that the invention is not restricted only to the examples presented above, but the invention may vary within the limits of the claims presented hereafter. Some possible embodiments of the invention are described in the dependent claims, and they are not to be considered to restrict the scope of protection of the invention as such.

The invention claimed is:

1. A method for a medication dispenser to obtain information from a medication package, comprising:
   providing an image of the medication package;
   wherein the method comprises:
   analysing the image to determine positions and formats of patterns in the image,
   selecting a layout, which has similar pattern formats in the same positions as the image, from a set of layouts stored in the medication dispenser, the selected layout defining the type of information for each pattern in the image, and
   interpreting the information contained in at least one of the patterns of the image by linking the content of the pattern to the type of information defined in the selected layout.

2. The method according to claim 1, wherein the step of providing an image of the medication package comprises:
   capturing with a camera at least one image of the medication package, and
   combining the at least one image into a single image.

3. The method according to claim 2, wherein the method comprises moving the medication package across an imaging area of the camera between the capturing of the images.

4. The method according to claim 2, wherein the method comprises illuminating with at least one light source the medication package.

5. The method according to claim 4, wherein the method comprises changing the intensity and/or the direction and/or the wavelength of the lighting.

6. The method according to 2, wherein the method comprises changing the position of the camera.

7. The method according to claim 1, wherein the step of providing an image of the medication package comprises receiving the image from a server over a communications network.

8. The method according to claim 1, wherein, if an error occurs in the step of selecting a layout, the method comprises:
   sending the image to a server over a communications network,
   generating, at the server, a new layout based on the image, and
   sending the new layout to the medication dispenser over a communications network.

9. The method according to claim 1, wherein one or more of the steps of analysing the image, selecting a layout and interpreting the information are carried out at a server that is communicatively connected to the medication dispenser over a communications network.

10. A medication dispenser, comprising:
    a container for holding a medication package containing medications to be taken at a predetermined taking time,
    means for transferring the medication package from the container to an outlet of the medication dispenser, and
    means for providing an image of the medication package;
    wherein the medication dispenser comprises a control unit that comprises:
    means for analysing the image to determine positions and formats of patterns in the image,
    means for maintaining a set of layouts in the medication dispenser,
    means for selecting a layout, which has similar pattern formats in the same positions as the image, from the set of layouts, the selected layout defining the type of information for each pattern in the image, and
    means for interpreting the information contained in at least one of the patterns of the image by linking the content of the pattern to the type of information defined in the selected layout.

11. The medication dispenser according to claim 10, wherein the means for providing an image of the medication package comprises a camera.

12. The medication dispenser according to claim 11, wherein the medication dispenser comprises at least one light source arranged to illuminate the medication package.

13. The medication dispenser according to claim 10, wherein the means for providing an image of the medication package comprises a communications unit for receiving the image from a server over a communications network.

14. The medication dispenser according to claim 10, wherein the medication dispenser comprises a detector arranged to detect the presence of the medication package in the container.

15. A method for a medication dispenser to obtain information from a medication package, comprising:
    obtaining an image of the medication package, the image of the medication package including at least two different patterns;
    analyzing the image of the medication package to determine both a format of each of the two patterns in the image of the medication package and a position of each pattern in the image of the medication package, the format of one of the patterns in the image of the medication package being a barcode and the format of the other pattern in the image of the medication package being text;
    selecting a layout from a set of layouts stored in the medication dispenser based on the image of the medication package, the selected layout having similar formats in the same corresponding positions as the formats in the image of the medication package, the selected layout defining the type of information for each pattern in the image of the medication package; and
    interpreting the information contained in at least one of the patterns of the image of the medication package by linking the content of the pattern to the type of information defined in the selected layout.

16. The method according to claim 15, wherein the barcode and the text are horizontally spaced apart from one another in a width direction of the image of the medication package.

17. The method according to claim 15, wherein the medication package includes perforations at a top edge and a bottom edge of the medication package, and one of the at least two patterns is positioned adjacent the top edge of the medication package and the other of the at least two patterns is positioned adjacent the bottom edge of the medication package.

* * * * *